US006420357B1

(12) United States Patent
Kashman et al.

(10) Patent No.: US 6,420,357 B1
(45) Date of Patent: Jul. 16, 2002

(54) CYTOTOXIC ALKALOID DERIVATIVES INCLUDING ASMARINE A AND B ISOLATED FROM A SPONGE

(75) Inventors: Yoel Kashman; Amira Rudi; Tesfamariam Yosief; Dolores G. Gravalos, all of Tres Cantos (ES)

(73) Assignee: Instituto Biomar, S.A., Onzonilla (ES)

( * ) Notice: Subject to any disclaimer, the term of this patent is extended or adjusted under 35 U.S.C. 154(b) by 0 days.

(21) Appl. No.: 09/582,181

(22) PCT Filed: Dec. 23, 1998

(86) PCT No.: PCT/US98/03884

§ 371 (c)(1),
(2), (4) Date: Jun. 22, 2001

(87) PCT Pub. No.: WO99/33832

PCT Pub. Date: Jul. 8, 1999

(30) Foreign Application Priority Data

Dec. 23, 1997 (GB) .............................................. 9727301

(51) Int. Cl.[7] ..................... C07D 487/06; A61K 31/505

(52) U.S. Cl. ....................................... 514/220; 540/556

(58) Field of Search ........................... 514/220; 540/556

(56) References Cited

FOREIGN PATENT DOCUMENTS

| WO | WO 92/00979 | 1/1992 |
| WO | WO 92/03438 | 3/1992 |

OTHER PUBLICATIONS

Hungarian Patent Office Novelty Seach Report Dated Dec. 7, 2001.
Faulkner et al., *Natural Product Rep.*, (1997), pp. 253–302.
Yosief et al., *Tetrahedron Letters*, "Asmarines A–C; Three novel cytotoxic metabolites from the marine sponge Raspailia sp.", (1998), vol. 39, pp. 3323–3326.
Nakamura et al., *Tetrahedron Letters*, "Agelasine–A, –B, –C And Novel Bicyclic Diterpenoids with A 9–Methyladeninium Unit Possessing Inhibitory Effects On Na, K–Atpase From The Okinawan Sea Sponge Agelas Sp"., (1984), vol. 25, pp. 2989–2992.
Bergeron et al., *Biochemical And Biophysical Research Communications*, "Sntineopllastic And Antiherpetic Activity Of Spermidine Catecholamide Iron Chelators", (1984), vol. 121, pp. 848–854.
Draetta, G. and Pagano, M. in "Annual Reports in Medicinal Chemistry, vol. 31", 1996, Academic Press, San Diego, pp. 241–246.*

* cited by examiner

Primary Examiner—Mukund J. Shah
Assistant Examiner—Thomas McKenzie
(74) Attorney, Agent, or Firm—Ernest V. Linek; Banner & Witcoff, Ltd.

(57) ABSTRACT

Disclosed are the compounds Asamarine A and B, novel cytotoxic diterpene-alkaloids, that have been isolated from the sponge Raspailia sp. The structure of these compounds have been established on the basis of NMR data and confirmed by X-ray analysis. Also disclosed are compounds (I) and (II), wherein wherein $R^1$ represents hydrogen or lower alkyl or lower alkanoyl; $R^2$ represents hydrogen or lower alkyl; $R^3$ is either an alkyl or a cycloalkyl group containing one or more isoprene units, or a monoterpene or a sesquiterpene or a sesquiterpene or a diterpene group; $R^4$ or $R^5$ represent hydrogen or lower alkyl; $R^6$ represents lower alkyl; and X represents F or Cl or Br or I.

Asamarine A

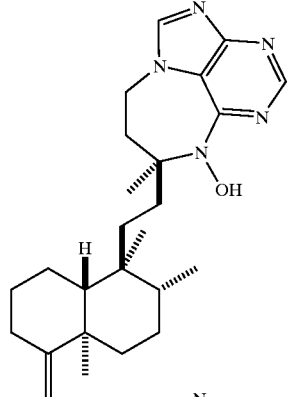

Asamarine B

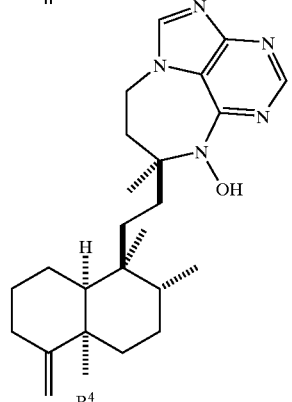

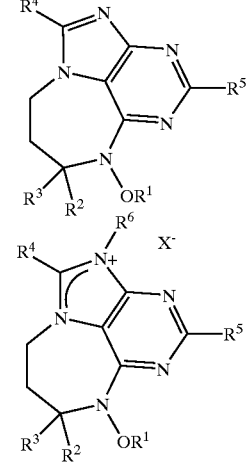

(I)

(II)

10 Claims, No Drawings

US 6,420,357 B1

CYTOTOXIC ALKALOID DERIVATIVES INCLUDING ASMARINE A AND B ISOLATED FROM A SPONGE

PRIORITY CLAIM

This application claims priority under 35 U.S.C. §119 of commonly owned PCT Application No. PCT/GB98/03884, filed Dec. 23, 1998. This application designated the United States and was published in the English language on Jul. 08, 1999 as WO 99/33832. The PCT application claims priority from British Patent Application No. GB 9727301.5, filed Dec. 23, 1997.

The present invention relates to new cytotoxic alkaloids, Asmarine A and B, isolated from the sponge Raspailia sp.

BACKGROUND OF THE INVENTION

Marine organisms, especially soft corals, sponges and tunicates, provide many secondary metabolites and exhibit a varying degree of biological activity (Reference 1). A family of these metabolites is the diterpene-alkaloid family; in 1984 (Reference 2) it was reported the structure of four Agelasines:

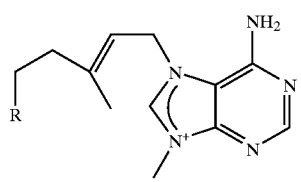

Agelasine A

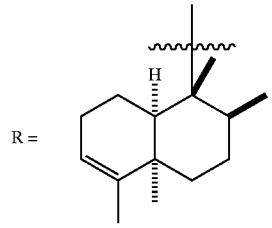

Agelasine B

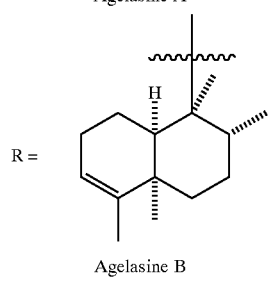

Agelasine C

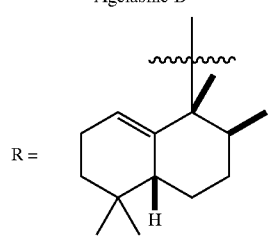

Agelasine D

We have isolated from the sponge Raspailia sp. new cytotoxic diterpene-alkaloids related to this agelasine family.

SUMMARY OF THE INVENTION

The present invention provides new diterpene-alkaloid having either the formula (I) or the formula (II):

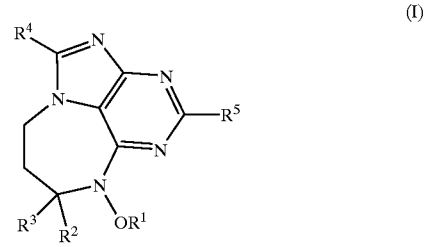

(I)

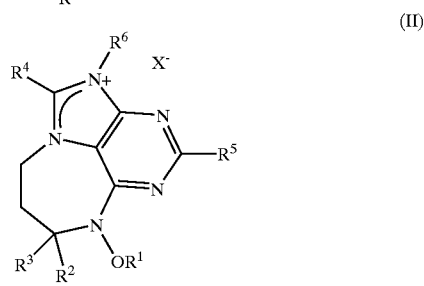

(II)

wherein $R^1$ represents hydrogen or lower alkyl or lower alkanoyl; $R^2$ represents hydrogen or lower alkyl; $R^3$ is either an alkyl or a cycloalkyl group containig one or more isoprene units, or a monoterpene or a sesquiterpene or a diterpene group; $R^4$ and $R^5$ represent hydrogen or lower alkyl; $R^6$ represents lower alkyl; X represents F or Cl or Br or I.

In the definitions of the groups in formulas (I) and (II), the lower alkyl and the lower alkyl moiety of the lower alkanoyl mean a straight-chain or branched alkyl group having 1 to 6 carbon atoms such as methyl, ethyl, propyl, isopropyl, butyl, isobutyl, sec-butyl, tert-butyl, pentyl, neopentyl and hexyl.

More particularly, the present invention relates to Asmarine A and Asmarine B, extracted and isolated from the sponge Raspailia sp. The structures of these compounds are the following:

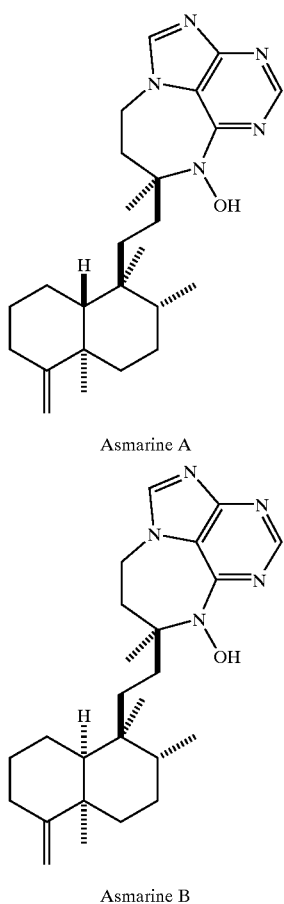

Asmarine A

Asmarine B

The stereochemistry showed is for a relative configuration in both cases. Asmarine A and Asmarine B exhibit antitumor activity. In particular, Asmarine A and Asmarine B exhibit antitumor activity against cell lines derived from human solid tumors, such as human lung carcinoma, human colon carcinoma and human melanoma, and, the like, it is active against other tumor cell lines, like leukemia and lymphoma.

The present invention also provides a method of treating a mammal affected by a malignant tumor sensitive to a compound with either the formula (I) or the formula (II), which comprises administering a therapeutically effective amount of the compound with either the formula (I) or the formula (II), or a pharmaceutical composition thereof. The present invention further provides pharmaceutical compositions which contain as active ingredient a compound with either the formula (I) or the formula (II), as well as a process for its preparation.

A further aspect of the invention is a method for preparing the compounds Asmarine A and Asmarine B, which comprises extraction and isolation from the sponge Raspailia sp.

Examples of pharmaceutical compositions include any solid (tablets, pills, capsules, granules, etc.) or liquid (solutions, suspensions or emulsions) with suitable formulation of oral, topical or parenteral administration, and they may contain the pure compound or in combination with any carrier or other pharmacologically active compounds. These compositions may need to be sterile when administered parenterally.

The correct dosage of a pharmaceutical composition comprising compounds with either the formula (I) or the formula (II), will vary according to the pharmaceutical formulation, the mode of application, and the particular situs, host and tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Antitumour Activity

Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serum (FCS), $10^{-2}$ M sodium bicarbonate and 0,1 g/l penicillin-G+streptomycin sulfate.

A screening procedure has been carried out to determine and compare the antitumor activity of these compounds, using an adapted form of the method described by Bergeron et al. (Reference 3). The antitumor cells employed were P-388 (suspension culture of a lymphoid neoplasm from DBA/2 mouse), A-549 (monolayer culture of a human lung carcinoma), HT-29 (monolayer culture of a human colon carcinoma) and MEL-28 (monolayer culture of a human melanoma).

P-388 cells were seeded into 16 mm wells at $1 \times 10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximately $IC_{50}$ was determined by comparing the growth in wells with drug to the growth in wells control.

A-549, HT-29 and MEL-28 cells were seeded into 16 mm wells at $2 \times 10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximately $IC_{50}$ was determined by comparing the growth in wells with drug to the growth in wells control.

The results of the in vitro cytotoxic assays for Asmarine A and Asmarine B with the cell lines P-388, A-549, HT-29 and MEL-28 are given in the following table:

| | $IC_{50}$ ($\mu$M) | | | |
|---|---|---|---|---|
| | P-388 | A-549 | HT-29 | MEL-28 |
| Asmarine A | 1.18 | 1.18 | 1.18 | 1.18 |
| Asmarine B | 0.24 | 0.12 | 0.12 | 0.24 |

Extraction and Isolation

Low-resolution mass spectra were recorded on a EIMS mass spectrometer. $^1$H and $^{13}$C-NMR spectra were recorded on a Bruker ARX-500 spectrometer. All chemical shifts are reported with respect to TMS ($\delta$=0 ppm).

Raspailia sp. (Rob Van Soest), (Class Demorspongia, Order poeciloscerida, Family Raspailiidea) was collected in Dahlak Archipelago, Eritrea by SCUBA diving to a depth of 23.5 m in May 1997. A reference sample is deposited in Tel Aviv University (ET-338). The sponge was frozen on site. The freeze dried sponge (20 gr) was extracted with ethyl acetate 2× to give a brown gum 1.2 g after evaporation. This brown gum was fractionated by Kupchon into four fractions: hexane, carbon tetrachloride, chloroform and water. The $CHCl_3$ and $CCl_4$ fractions were similar. These two fractions were combined and chromatographed on a sephadex LH-20 column eluting with MeOH:$CHCl_3$ (1:1) giving five fractions. Fractions (3–5) were further chromatographed repeatedly on a sephadex LH-20 with the same solvent system yielding Asmarine A (100 mg) as a solid, mp=232° C., m/z+=423 ($C_{25}H_{37}N_5O$), (100%) 188 ($C_8H_6N_5O^+$), $[\alpha]_D^{20}$+ 55° (c=0.5, $CHCl_3$), IR 3400, 2928, 1600, 1553, 1451, 1400, 1388, 900 cm$^{-1}$, the structure of this Asmarine A was confirmed by X-ray analysis. With the same solvent was also isolated Asmarine B (120 mg) as an oil, m/z+=423 ($C_{25}H_{37}N_5O$), (100%) 188 ($C_8H_6N_5O^+$), $[\alpha]_D^{20}$.+60° (c=0.5, $CHCl_3$), IR 3400, 2927, 1606, 1553, 1451, 1404, 1388, 900 cm$^{-1}$.

For NMR data of Asmarine A and B see next Table: in all cases the solvent is $CDCl_3$ and all chemical shifts are reported with respect to TMS (δ=0 ppm).

| | $\delta_C$ | | $\delta_H$ | |
|---|---|---|---|---|
| C No. | Asmarin A | Asmarine B | Asmarine A | Asmarine B |
| 1 | 21.82 t | 21.17 t | 1.70 d, 1H | 1.82 m, 2H |
| | | | 1.45 m, 1H | |
| 2 | 28.56 t | 24.13 t | 1.85 brd, 1H | 1.75 m, 1H |
| | | | 1.21 m, 1H | 1.60 m, 1H |
| 3 | 33.20 t | 31.65 t | 2.25 dt, 1H | 2.45 m, 1H |
| | | | 2.05 dd, 1H | 2.12 m, 1H |
| 4 | 160.59 s | 153.65 s | | |
| 5 | 40.05 s | 39.35 s | | |
| 6 | 37.24 t | 38.12 t | 1.50 m, 2H | 2.10 t, 1H |
| | | | | 1.20 t, 1H |
| 7 | 27.36 t | 27.22 t | 1.45 m, 2H | 1.54 m, 1H |
| | | | | 1.20 m, 1H |
| 8 | 36.68 d | 38.12 d | 1.37 m, 1H | 1.35 m, 1H |
| 9 | 39.26 s | 40.54 s | | |
| 10 | 48.62 d | 46.56 d | 1.05 d, 1H | 1.39 m, 1H |
| 11 | 31.23 t | 31.05 t | 1.55 dt, 1H | 1.59 m, 1H |
| | | | 1.25 m, 1H | 1.30 t, 1H |
| 12 | 33.01 t | 31.55 t | 1.95 dt, 1H | 1.95 dt, 1H |
| | | | 1.43 m, 1H | 1.55 m, 1H |
| 13 | 64.20 s | 64.95 s | | |
| 14 | 36.68 t | 36.40 t | 2.50 dt, 1H | 2.55 m, 1H |
| | | | 2.15 dd, 1H | 2.25 m, 1H |
| 15 | 42.30 t | 42.33 t | 4.25 dt, 1H | 4.30 t, 2H |
| | | | 4.20 dd, 1H | |
| 16 | 21.75 q | 23.09 q | 1.44 s, 3H | 1.49 s, 3H |
| 17 | 15.93 q | 15.84 q | 0.70 d, 3H | 0.74 d, 3H |
| 18 | 102.45 t | 105.69 t | 4.60 s, 2H | 4.70 d, 2H |
| 19 | 20.08 q | 32.87 q | 1.00 s, 3H | 1.11 s, 3H |
| 20 | 18.28 q | 19.85 q | 0.65 s, 3H | 0.82 s, 3H |
| 2' | 151.68 d | 151.64 d | 8.50 s, 1H | 8.50 d, 1H |
| 4' | 149.00 s | 149.57 s | | |
| 5' | 109.31 s | 109.32 s | | |
| 6' | 158.70 s | 158.38 s | | |
| 8' | 143.10 d | 143.32 d | 7.95 s, 1H | 7.95 s, 1H |

REFERENCES

1. Faulkner, D. *Nat. Prod. Rep.* 1997, 14, 259–302 and references therein.
2. Nakamura, H. et al. *Tetrahedron Lett.* 1984, 25, 2989–2992
3. Raymond J. Bergeron, Paul F. Cavanaugh, Jr., Steven J. Kline, Robert G. Hughes, Jr., Gary T. Elliot and Carl W. Porter. Antineoplastic and antiherpetic activity of spermidine catecholamide iron chelators. *Biochem. Bioph. Res. Comm.* 1984, 121, 848–854.

What is claimed is:

1. A compound having either the formula (I) or the formula (II):

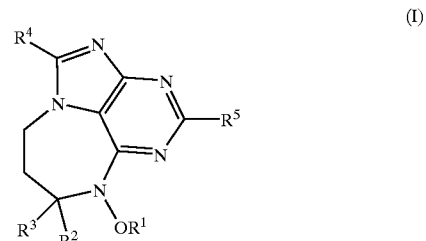

(I)

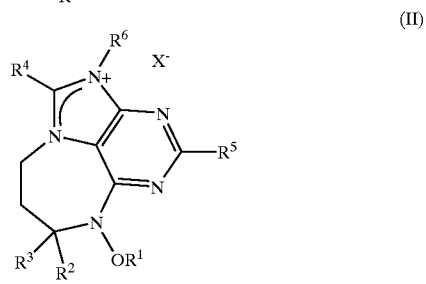

(II)

wherein $R^1$ represents hydrogen or lower alkyl or lower alkanoyl;

$R^2$ represents hydrogen or lower alkyl;

$R^3$ represents a group of formula

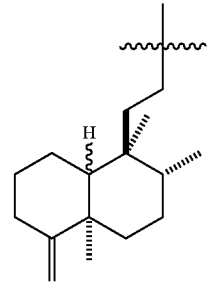

$R^4$ and $R^5$ represent hydrogen or lower alkyl;

$R^6$ represents lower alkyl; and

X represents F or Cl or Br or I.

2. A compound, Asmarine A, according to claim 1, having the following formula:

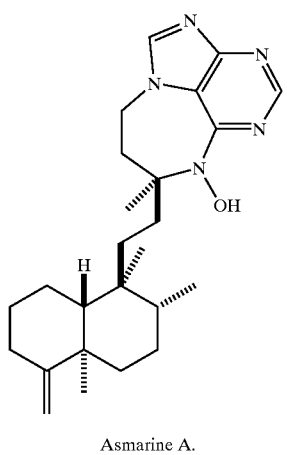

Asmarine A.

3. A compound, Asmarine B, according to claim 1, having the following formula:

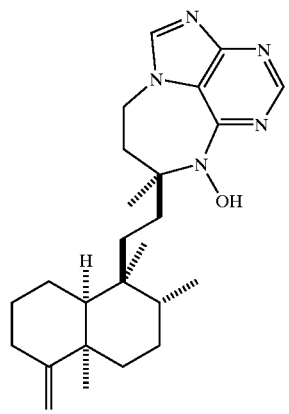

Asmarine B.

4. A method of treating a mammal affected by a malignant tumor selected from lymphoma, lung carcinoma, colon cancer and melanoma, which comprises administering to the affected individual a therapeutically effective antitumor amount of a compound of formula (I) or formula (II), as defined in claim 1, or a pharmaceutical composition thereof.

5. A method according to claim 4, wherein the compound of formula (I) or (II) is Asmarine A (as defined in claim 2) or Asmarine B (as defined in claim 3).

6. A pharmaceutical preparation which contains as active ingredient a compound of formula (I) or formula (II), as defined in claim 1.

7. A pharmaceutical preparation according to claim 6, wherein the compound of formula (I) or (II) is Asmarine A (as defined in claim 2) or Asmarine B (as defined in claim 3).

8. A method of treating a mammal affected by a malignant tumor selected from lymphoma, lung carcinoma, colon cancer and melanoma, which comprises administering to the affected individual a therapeutically effective antitumor amount of a compound of formula (I) or (II), as defined in claim 1, together with one or more additional antitumoral compounds.

9. A method according to claim 8, wherein the compound of formula (I) or (II) is Asmarine A (as defined in claim 2) or Asmarine B (as defined in claim 3).

10. A method for preparing a compound selected from Asmarine A (as defined in claim 2) or Asmarine B (as defined in claim 3), comprising the steps of:

(a) extracting the crude compound from the sponge Raspailia sp. using a solvent of suitable polarity; and (b) isolating the compound from the crude extract obtained in step (a) using a suitable chromatographic method.

* * * * *